(12) United States Patent
Nörenberg

(10) Patent No.: US 7,739,057 B2
(45) Date of Patent: Jun. 15, 2010

(54) METHOD AND APPARATUS FOR MEASURING THE RATE OF PERMEATION OF GASES AND VAPOURS THROUGH MATERIALS

(75) Inventor: Holger Nörenberg, Oxford (GB)

(73) Assignee: Technolox Ltd., Oxford (GB)

( * ) Notice: Subject to any disclaimer, the term of this patent is extended or adjusted under 35 U.S.C. 154(b) by 1340 days.

(21) Appl. No.: 10/776,696

(22) Filed: Feb. 12, 2004

(65) Prior Publication Data

US 2004/0225457 A1  Nov. 11, 2004

(30) Foreign Application Priority Data

Feb. 13, 2003 (GB) .................................. 0303230.7

(51) Int. Cl.
G01N 31/00 (2006.01)

(52) U.S. Cl. ...................................................... 702/24

(58) Field of Classification Search .................. 702/24, 702/51; 73/38; 250/282, 286; 429/54; 356/338
See application file for complete search history.

(56) References Cited

U.S. PATENT DOCUMENTS

| | | | |
|---|---|---|---|
| 6,629,043 B1 * | 9/2003 | Poteat .......................... 702/51 |
| 6,766,682 B2 * | 7/2004 | Engle et al. ..................... 73/38 |
| 2002/0189325 A1 * | 12/2002 | Bowen et al. ................... 73/38 |
| 2003/0001086 A1 * | 1/2003 | Noerenberg et al. ......... 250/282 |
| 2004/0123646 A1 * | 7/2004 | Echigo et al. ................... 73/38 |
| 2005/0079404 A1 * | 4/2005 | Schubert et al. ............... 429/54 |
| 2005/0092068 A1 * | 5/2005 | Ascheman et al. .............. 73/38 |

* cited by examiner

Primary Examiner—Tung S Lau
Assistant Examiner—Xiuquin Sun

(57) ABSTRACT

A method and an apparatus are provided for measuring the rate of permeation using a mass spectrometer as detector. The gas container containing the test sample is filled with a gas or vapor inside a filling chamber. A pressure-compensating device attached to the gas container alleviates the effect of pressure decrease inside the gas container due to permeation. After transferring the test sample to the investigation chamber the partial pressure of the gas or vapor is detected after permeation through the test sample. After calibration the measured partial pressure is converted into the rate of permeation. The rate of permeation can be studied position-resolved at different locations on the sample. The method can be used to measure permeation through film samples, edges or complete devices.

50 Claims, 5 Drawing Sheets

METHOD AND APPARATUS FOR MEASURING THE RATE OF PERMEATION OF GASES AND VAPOURS THROUGH MATERIALS

CROSS-REFERENCE TO RELATED APPLICATIONS

This application is based upon and claims the benefits of priority from the prior UK patent application entitled: "Method and apparatus for measuring the rate of permeation of gases and vapours through barriers and other materials" no. 0303230.7 filed 13 Feb. 2003. The content of this application is incorporated by reference.

BACKGROUND OF THE INVENTION

1. Field of the Invention

The present invention relates to the measurement of the rate of permeation of a gas or vapour or a mixture of a gas and a vapour through a sample of a material (polymer, metal, ceramic material, composite, semiconductor, biological material or a combination thereof).

2. Description of the Related Art

US 2003/0001086A1

US 2002/0173922A1

U.S. Pat. No. 5,390,530

JP63132137

EP 1373861

Nörenberg, H. et al.: Review of Scientific Instruments 70 (1999) 2414-2420.

Permeation is the transmission of molecules and atoms through samples. Measuring the rate of permeation of vapours and gases through materials, in particular barrier materials, is important in various fields. Examples include packaging of food, medical supplies, electronic components and components in fuel cells and fuel tanks. Barrier layers serve the purpose of preventing or restricting the passing of a gas or vapour.

A number of methods are known to measure the rate of permeation using infrared sensors, electrochemical sensors, optical sensors or pressure sensors. Mass spectrometric methods, methods using a calcium layer ("Calcium test") and methods using radioactive tracers are known too.

The known applications using infrared, electrochemical, total pressure or optical sensors are limited with respect to their sensitivity. The Calcium test is limited to species, which undergo a chemical reaction with the calcium layer. Radioactive tracer methods are limited to a very restricted number of radioactive isotopes available, whose handling is very cumbersome and potentially dangerous due to their radioactive nature.

In some known mass spectrometric application a gas cell is filled with an amount of liquid and then introduced into a vacuum chamber. After some time a saturated atmosphere is established inside a gas cell, which contains vapour at the partial pressure of the liquid. In the case of water and water vapour a relative humidity of 100% is established inside the gas cell. This method creates a number of difficulties and limitations.

The vapour pressure of a vapour in an enclosed volume above its liquid phase is unequivocally linked to its temperature by thermodynamic law. Consequently, the vapour pressure generated above a liquid phase in equilibrium and the temperature cannot be varied independently. This unequivocal link between temperature and vapour pressure means, that at different temperatures the said vapour pressure is different. The vapour pressure of water vapour varies exponentially between about 2340 Pa at a temperature of 20° C. (293K) and 101300 Pa at a temperature of 100° C. (373K). This represents a 43-fold increase in the water vapour pressure at a less than twofold increase of the absolute temperature.

It is certainly desirable to test samples under conditions, which they may encounter in practical use. For instance mobile phones containing organic light-emitting (OLED) displays will be used in different climates. Therefore testing the display under hot and humid conditions as well as testing under hot and dry conditions is desirable.

It is an disadvantage of the known method that the temperature cannot be varied at a given water vapour pressure or that at a given temperature the water vapour pressure cannot be varied. A further disadvantage is, that the known method does not allow compensating for the increased pressure at elevated temperatures, which may cause undesirable mechanical stress, which may damage the sample.

In known applications a gas cell is filled with a gas. The signal measured with a mass spectrometer decays as the gas cell is depleted of gas caused by permeation. The decay of the signal can be approximated by exponential functions to extract the rate of permeation. This method is impractical, cumbersome and inaccurate, as the exponential parameters have to be determined for each permeating species.

In known applications the sample is mounted flat in a gas cell. This limits the sample to simple shapes such as sheet material. More complicated structures containing materials of different permeability, including complete electronic devices such as batteries, or sub-assemblies of devices including their edges, are impossible to test in this arrangement Most conventional methods measure the average rate of permeation of the sample. The disadvantage is that they do not provide information about whether the permeation through the sample is homogeneous or varies across the sample due to defects, other inhomogeneities or areas of different permeability of the sample, which are put there on purpose.

BRIEF SUMMARY OF THE INVENTION

According to the present invention a method and an apparatus of measurement of the rate of permeation of gases and vapours through a test sample to alleviate the problems described above is presented. "Gas container" describes a vessel that can contain a gas or a vapour or a mixture thereof.

In the first aspect of the invention a method and an apparatus are provided to measure the rate of permeation of a gas or vapour through a test sample under constant pressure conditions:

filling a gas container containing the test sample with an amount of vapour or gas or vapour mixture thereof inside a filling vacuum chamber transferring the gas container with the test sample to a vacuum chamber with vacuum and arranging the gas container in a way that the test sample faces a mass spectrometer to measure the partial pressure of the gas or vapour species after permeation through the test sample using a specially formed gas container with a volume adjustable device to compensate for the depletion of gas or vapour due to permeation through the test sample concluding the rate of permeation from the measured partial pressure and calibration measurements or reference values.

The first aspect of the invention has the main advantage, that the pressure decrease inside the gas container due to permeation is eliminated or greatly reduced. It is an advantage too that the gas container can be filled with gas or vapour over a wide pressure range, in the case of a vapour up to its vapour pressure. Another advantage is the exclusion of ambient gas from the interior of the gas container. The advantage of filling the gas container with a gas or vapour at a low pressure is, that it reduces the stress acting on the sample. Stress is caused by the pressure difference between the inside of the gas container and the vacuum of the vacuum system.

The rate of permeation of the test sample is estimated including a calibration procedure, where one or more samples with a known rate of permeation are measured. The rate of permeation of the unknown test sample is then extrapolated from these values by using the measured partial pressure of the gas or vapour after permeation through the test sample. The advantage of using a calibration procedure is that it gives an absolute value of the rate of permeation. The advantage of using a calibration procedure involving a number of samples with a known rate of permeation is its increased accuracy.

In the second aspect of the invention a method and an apparatus are provided to measure the rate of permeation of water vapour through a test sample comprising:
 filling the gas container containing the test sample with an amount of water vapour at the desired relative humidity inside a filling chamber
 transferring the gas container with the test sample to a vacuum chamber with vacuum and arranging the gas container in a way that the test sample faces a mass spectrometer to measure the partial pressure of the water vapour after permeation through the test sample
 concluding the rate of permeation of water vapour from the measured partial pressure
 increasing the sensitivity of the experiment by including water isotopes $D_2^{16}O$, $D_2^{17}O$, $D_2^{18}O$, $H_2^{16}O$, $H_2^{17}O$, $H_2^{18}O$ with a low signal in the background pressure spectrum in the UHV-chamber.

The advantage of the second aspect is the possibility to test samples under conditions that require a relative humidity of 100% or less. The relative humidity inside the gas container can be adjusted by using saturated solutions, in particular salt solutions. The advantage of this method is its simplicity.

The advantage of using a gas container with an integrated vapour reservoir is, that the vapour pressure inside the gas container can be adjusted either during filling or by combining this method with a device that allows changing the inner volume of the gas container as described in the first aspect without removal from the vacuum system under vacuum and without disrupting the experiment. Yet another advantage is the exclusion of ambient gas from the interior of the gas container. The advantage of using water vapour isotopes with a low background pressure is an improved signal to noise ratio. The advantage of filling the gas container with water vapour at a relative humidity of less than 100% is, that it reduces the pressure difference acting on the sample during the experiment and hence the mechanical stress acting on the test sample.

In the third aspect of the invention a method and an apparatus are provided to measure the rate of permeation of gases or vapours or mixtures thereof through complete devices or sub-assemblies thereof or through the edge of a film sample comprising:
 a means for filling the device or sub-assembly with the gas or vapour of interest
 a means of transferring and positioning the test sample (as described in the 1$^{st}$ and 2$^{nd}$ aspects)
 a sample holder to manipulate the test sample in the vacuum chamber The advantage of the third aspect of the invention is that cumbersome preparations of proxy test samples, which are made to fit the measurement kit of the respective method, are not necessary. Test samples can be tested in the shape of their final application. This is of advantage because not all samples can be prepared in a suitable shape for conventional permeation measurements.

In the fourth aspect of the invention a method and an apparatus are provided to study the rate of permeation of gases or vapours or a mixture thereof through samples position-resolved at different locations on the test sample comprising:
 a device to guide (to the mass spectrometer) gas or vapour molecules coming from the region of interest on the test sample
 a means to move the gas container with the test sample and the mass spectrometer with respect to each other to expose different regions on the test sample to the mass spectrometer
 an enclosure of the mass spectrometer, which can be, pumped separately having an entrance hole diameter of around 5 mm or less.

The advantage of this aspect is, that it allows to study the rate of permeation position-resolved on the test sample and to test the lateral homogeneity of the sample. Another advantage is, that a number of test samples can be mounted on a gas container with reservoirs containing different gases or vapours under different conditions (for example at different pressures) such significantly increasing throughput of test samples. Yet another advantage of such a method being available is, that test samples can be investigated, which use locally varying rates of permeation to achieve effects such as controlled drug release.

BRIEF DESCRIPTION OF THE SEVERAL VIEWS OF THE DRAWINGS

A method as specific embodiment of the invention will now be described by way of non-limiting example with reference to the accompanying drawings in which.

DETAILED DESCRIPTION OF THE INVENTION

Concerning the first aspect of the invention an experiment may be carried out as follows: The purpose of the experiment is the measurement of the rate of permeation of a gas or a vapour through a test sample.

Figure 1:
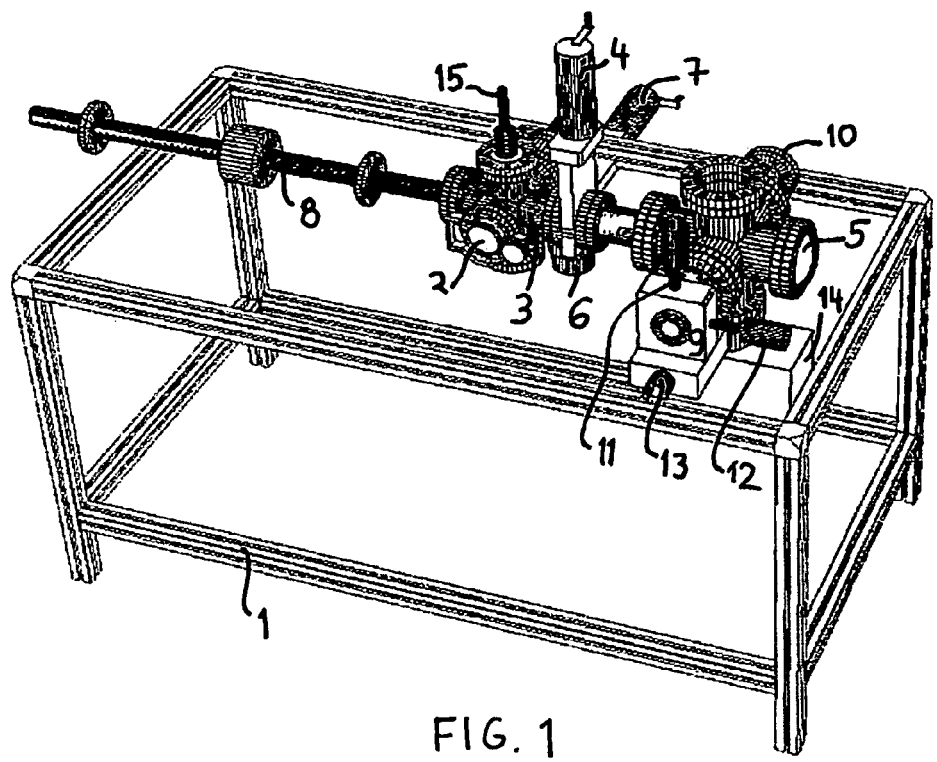
FIG. 1 shows a perspective view of the apparatus used in the method

FIG. 1 shows the ultra-high vacuum (UHV) apparatus used for the method mounted onto a frame 1. A gas container is introduced through the door 2 into the filling chamber 3. During this operation the gate valve 4 is closed to keep the investigation chamber 5 under vacuum. The door 2 is then closed and the filling chamber 3 is evacuated by means of a turbomolecular pump 6 backed by a two-stage rotary pump (not shown) with the gate valve 7 open. After reaching a sufficiently low vacuum in the filling chamber 3, the gate valve 7 is closed and the gas or vapour of interest is admitted to the filling chamber 3 (explained in more detail below).

After filling is completed, the filling chamber 3 is evacuated by means of the turbomolecular pump 6 with the gate valve 7 open. After reaching a sufficiently low vacuum in the filling chamber 3 the gas container with the sample and filled with the gas or vapour will be transferred into the investigation chamber 5 by means of a transfer arm 8. The transfer arm can be used to hold the sample after introduction in the filling chamber 3 and in conventional design allows for translational motion along its axis as well for rotation around its axis. The gas container is put on a xyz-stage 9; the transfer 8 arm is then withdrawn to its original position and the gate valve 4 closed. The gas container will be positioned to face the mass spectrometer 10 by means of three positioning screws 11, 12 and 13, which allow movement in the x-, y- and z-directions. For increased accuracy these screws could be micrometer screws. An alternative embodiment is using stepper motors instead of the positioning screws for greater ease of operation. The investigation chamber is kept under vacuum by means of a pump, which in this embodiment is an ion pump 14. For convenience of operation a manipulating device 15 is fitted to the filling chamber 3. Using conventional methods the temperature of the gas container can be changed by heating or cooling.

After positioning the sample the partial pressure of the gases or vapours of interest will be monitored by means of the mass spectrometer 10 and the output signal of the mass spectrometer will be recorded on a conventional personal computer. The partial pressure measured by the mass spectrometer is used to derive the rates of permeation. This can be done for individual species or for groups of several species of the gas or vapour.

The method of deriving permeation rates will be described in greater detail now. Under suitable experimental conditions the partial pressure detected by the mass spectrometer will assume a constant value after some time. This value of the partial pressure is a measure for the rate of permeation of the test sample. In order to quantify the rate of permeation a calibration process is carried out. A range of samples is selected and the rate of permeation through these samples is established by conventional methods including MOCON Permatran, Oxtran and the time-lag method. If conventional methods are not available, known values from the literature may be used. The same samples are investigated with the mass spectrometric method described herein and the measured partial pressure is then related to the values obtained by conventional methods.

Figure 2:
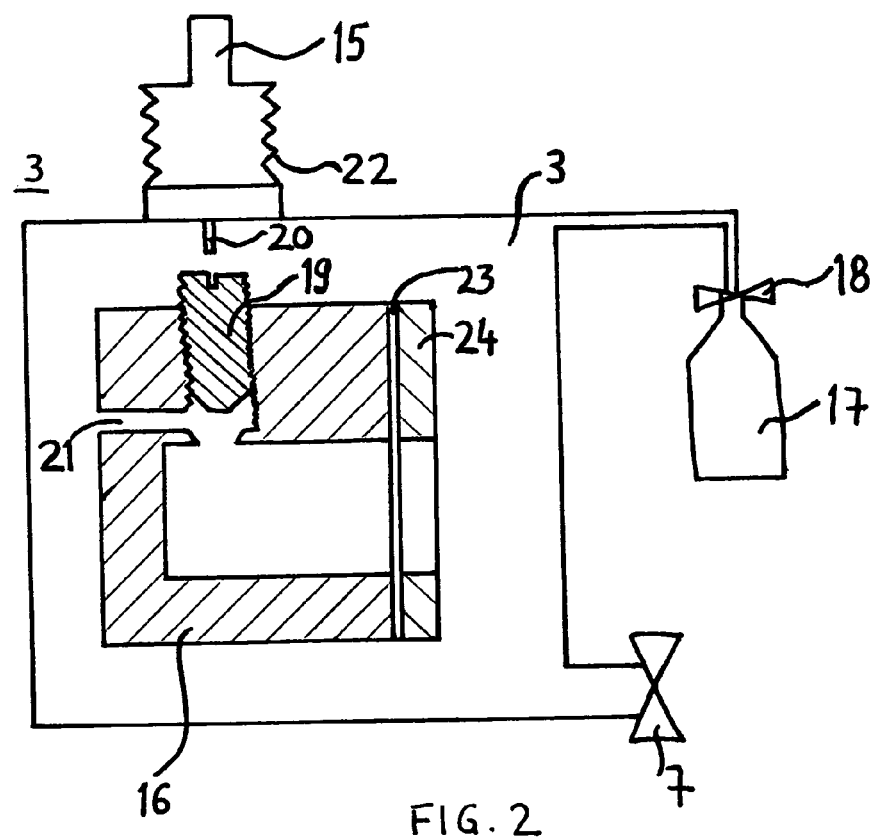
FIG. 2 shows a diagrammatic view of the filling chamber containing a gas container

FIG. 2 shows details related to the filling procedure of the gas container 16 inside the filling chamber 3 with a gas or vapour. The filling chamber is under vacuum. A vessel 17 containing the gas or vapour of interest is separated from the filling chamber 3 by a valve 18. After opening the valve 18 the filling chamber 3 fills up with the gas or vapour to a certain pressure, which may be monitored by a pressure sensor (not shown). The gas container 16 contains a valve 19, which in the current embodiment is a threaded piece with a conically shaped end running in a threaded hole. Moving the threaded piece up (with reference to the orientation shown in FIG. 2) by means of a manipulating device 15 acting as a screwdriver 20 engaging the valve 19, allows gas or vapour from inside the filling chamber 3 to enter the gas container 16 through the hole 21. After a sufficient period of time the interior of the gas container 16 is at the same pressure as the interior of the filling chamber 3. Moving the threaded piece 19 down closes the gas container 16 and no more gas or vapour can enter or leave it. For a more flexible handling a flexible hose or a bellow 22 can be used to attach the manipulating device 15 to the filling chamber 3. The sample 23 is attached to the gas container 16 by means of a lid 24. Gas containers containing more than one sample, each of which covers one opening and has one threaded piece for filling can be easily implemented as extension of the design shown in FIG. 2.

Figure 3:
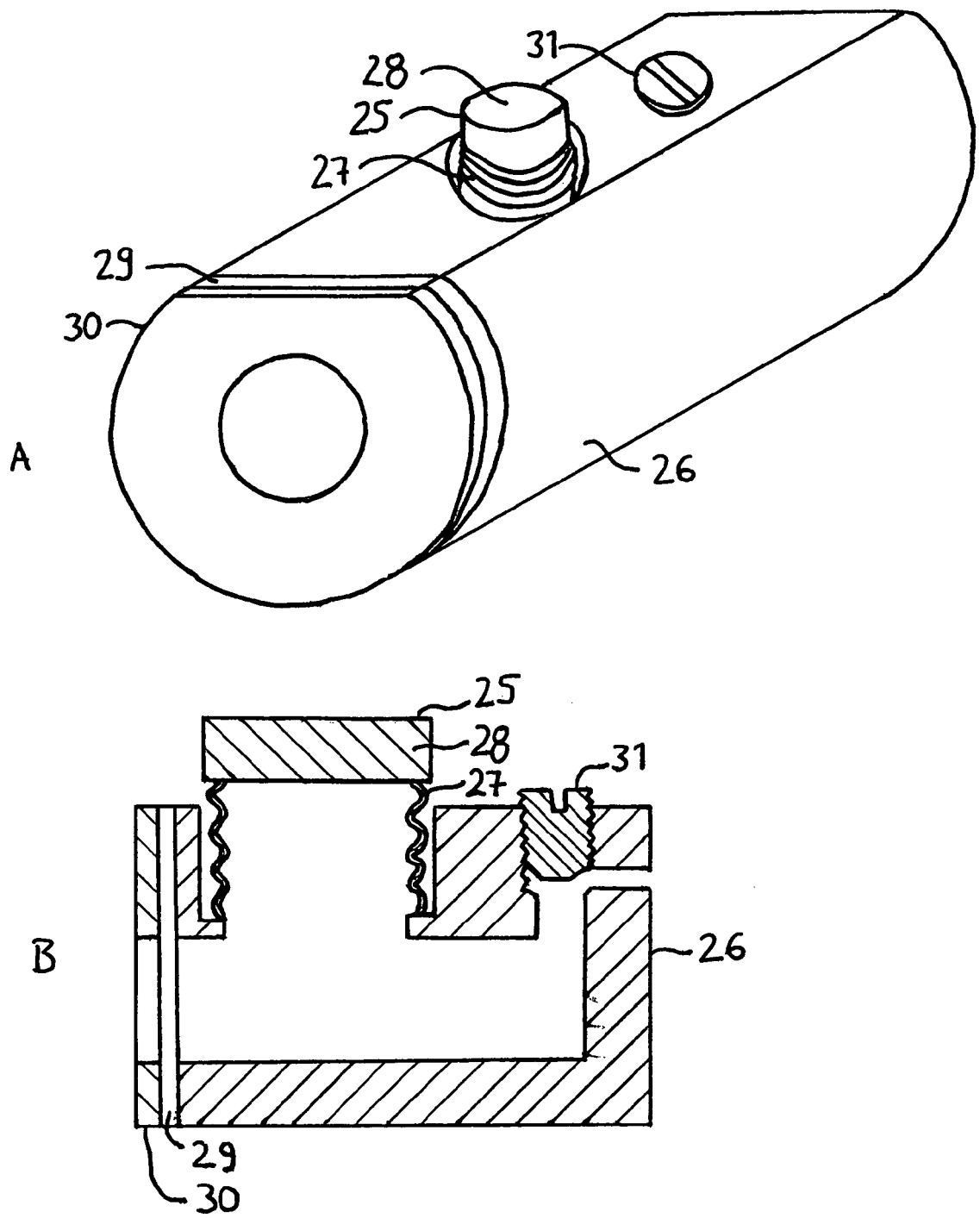
FIG. 3 shows a gas container with pressure compensating device
 A) perspective view
 B) cross-sectional view of A) in a plane comprising the directions perpendicular to the sample and perpendicular to the flat on the cylindrical part.

FIG. 3 shows a pressure-compensating device 25 attached to the gas container 26. The pressure-compensating device 25 serves the purpose of maintaining a constant pressure inside the gas container 26. It is part of the gas container 26 and is made of a flexible bellow 27 with a top 28 joined to the bellow 27. In addition to serving the purpose of keeping a constant pressure inside the gas container, it can also be used to change the pressure inside the gas container during a measurement.

The weight force of the top 28 of the bellow 27 acts on the gas inside the gas container 26. In a vacuum chamber with vacuum the gas or vapour pressure inside the gas container 26 will be this weight force divided by the effective area of the top 28 provided the spring force of the bellow 27 is much less than the weight force exercised by the top 28. This can be achieved by using thin lamellas for the bellow of 0.1 mm thickness or thinner and operating the bellow 27 around its free length. To keep the volume of the top 28 as small as possible, the main part of the top 28 may be made of an UHV-compatible material with a high density such as tungsten. The effect of the weight force of the top 28 is maximised by arranging the gas container with the normal of the top 28 parallel to the direction of maximum gravity. The size of the bellow 27 and the thickness and shape of its top 28 can be adjusted for the prevailing experimental parameters such as the required pressure difference. FIG. 3 shows a sample 29 attached to the gas container by means of a lid 30 and a threaded piece 31 for filling.

The bellow 27 with the top 28 can easily be used to change the pressure inside the gas container 26 during the experiment by pushing it or pulling it by means of a pin operated on the vacuum system by conventional means such as a vacuum feedthrough. A mechanical guide of conventional design such as a piece of appropriate tubing can be used to aid the bellow. Conventional means such as attaching a thermal conductor to the gas container can be used to change the temperature of the sample to measure the rate of permeation over a range of temperatures, including cryogenic temperatures.

Concerning the second aspect of the invention the method may be used as follows:

The purpose of the experiment is to measure the rate of water vapour permeation through a test sample.

The sample transfer proceeds in the same or a similar way as described in the first aspect of the invention.

To achieve different degrees of humidity inside the gas container a number of conventional methods can be used. Saturated salt solutions create atmospheres of a constant humidity below 100% relative humidity. The examples given for the relative humidity established over saturated salt solutions at 25° C. show that a large range of relative humidity can be covered, with further solutions available to generate a great number of other levels of relative humidity.

| | |
|---|---|
| Lithium chloride | 11.3% |
| Sodium chloride | 75.3% |
| Potassium Nitrate | 93.6% |

A saturated salt solution placed inside a gas container of conventional design will at a given temperature after sufficient time produce a constant relative humidity above the salt solution. To avoid contact with the samples a small plastic tray with a large opening can be used to contain the salt solution inside the gas container.

Figure 4:
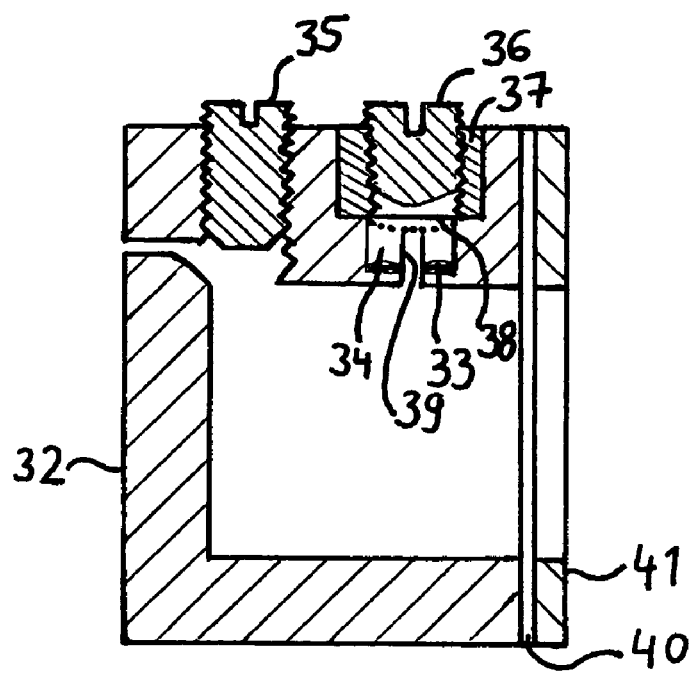
FIG. 4 shows in sectional view a gas container with vapour reservoir

To measure the rate of permeation of water vapour through a sample in the absence of ambient gases, an experiment can be carried out as follows:

FIG. 4 shows a gas container 32 containing a vapour reservoir with liquid water 33 and its water vapour phase 34. Before the gas container 32 is filled with water vapour 34 from the reservoir of liquid water 33, the gas container 32 is evacuated according to the procedure described in the first aspect of the invention. A threaded piece 35 to connect and disconnect the interior of the gas container 32 from its surrounding is shown for convenience.

The water vapour 34 can be separated from the interior of the gas container 32 by means of a valve. The valve consists of a screw 36, an insert 37 and a disk 38. The purpose of the screw 36 is to act on the disk 38 to push it from its free position (solid line) into its extended position (dotted line). The purpose of the insert 37, which may be screwed or pushed into the gas container 32 is to keep the disk 38 in place to prevent gas or vapour from moving between the space above the disk 38 and the space below it. The disk 38 is made of a material with low permeability and sufficient elasticity such as nickel or VITON. In the closed position when the disk 38 is pushed against the tube 39 by means of the screw 36 (dotted line) the vapour in the vapour reservoir 34 cannot enter the interior of the gas container 32. This is the position for evacuating the interior of the gas container 32 before filling with water vapour.

After the interior of the gas container 32 is evacuated, it is then disconnected from the vacuum of the filling chamber 3. The interior of the gas container 32 is filled with water vapour by retracting the screw 36 such releasing the disk 38 from its extended position. Vapour from the vapour reservoir 33 enters the interior of the gas container 32 through the tube 39.

After sufficient vapour has entered, the screw 36 is moved to push the disk 38 against the tube 39 forming a seal such preventing any further vapour entering the interior of the gas container 32. The liquid phase 31 should be kept in a sponge or similar device to prevent violent boiling. A pressure-compensating device 27 as shown in FIG. 3 can be added to the gas container and is omitted here for clarity. Vapour sources such as other liquids or salt solutions may be used in a similar way. FIG. 4 shows a sample 40 attached to the gas container 32 by means of a lid 41.

Usually, the small amount of ambient gas that remains in the volume of the water vapour 34 after filling under ambient conditions is negligible as the volume 34 is much smaller than the volume of the interior of the gas container 32. Increased accuracy can be achieved by purging the gas container 32 under vacuum conditions.

In the case of water vapour, using different isotopes of water such as $D_2^{16}O$, $D_2^{17}O$, $D_2^{18}O$, $H_2^{16}O$, $H_2^{17}O$, $H_2^{18}O$ for the water vapour reservoir makes it possible to enhance the sensitivity of the mass spectrometric estimation by choosing a mass-to-charge ratio where the background for the given sample is lowest. In most application the background at mass number 22 will be lowest and $D_2^{18}O$, known as "doubly labelled water" may be used.

Concerning the third aspect of the invention the measurement may be carried out as follows:

The purpose of the experiment is, to measure the rate of permeation through samples other than film or through the edge of a film sample. As the sample shapes may vary over a wide range the illustration is limited to one example.

Figure 5:
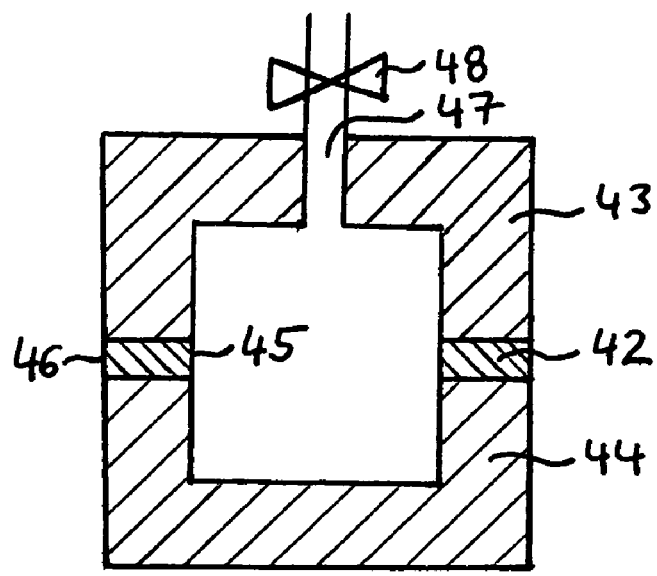
FIG. 5 shows in sectional view a gas container used to investigate edge permeation

FIG. 5 shows a gas container to study edge permeation. A sample 42 is clamped between an upper part 43 and a lower part 44. The gas or vapour enters the sample through its inner edge 45 then permeates through the sample 42 and leaves it at its outer edge 46 which are positioned to face the mass spectrometer. The sample 42 may be a resin, such as an epoxy resin, which glues together the lower part 43 and the upper part 44. Filling with gas or vapour may proceed through an opening 47 with a valve 48 according to the procedure described in the first and second aspects. Edge permeation through complete devices such as lithium batteries can be studied in similar way.

Concerning the fourth aspect of the invention an experiment may be carried out as follows:

The purpose of the experiment is to study the rate of permeation position-resolved on different locations on a test sample.

Figure 6:
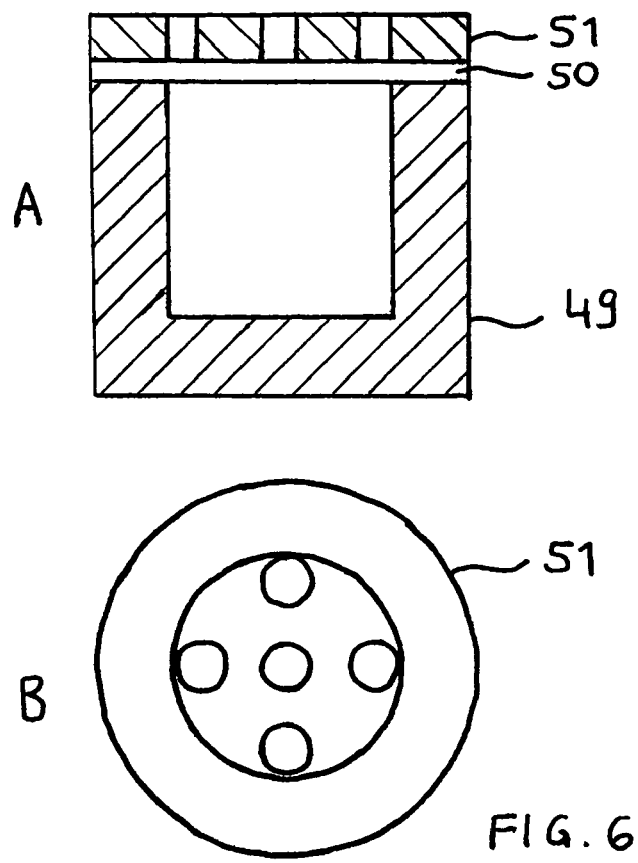
FIG. 6 shows in diagrammatic view the relative position between the mass spectrometer and the gas container
Figure 7:
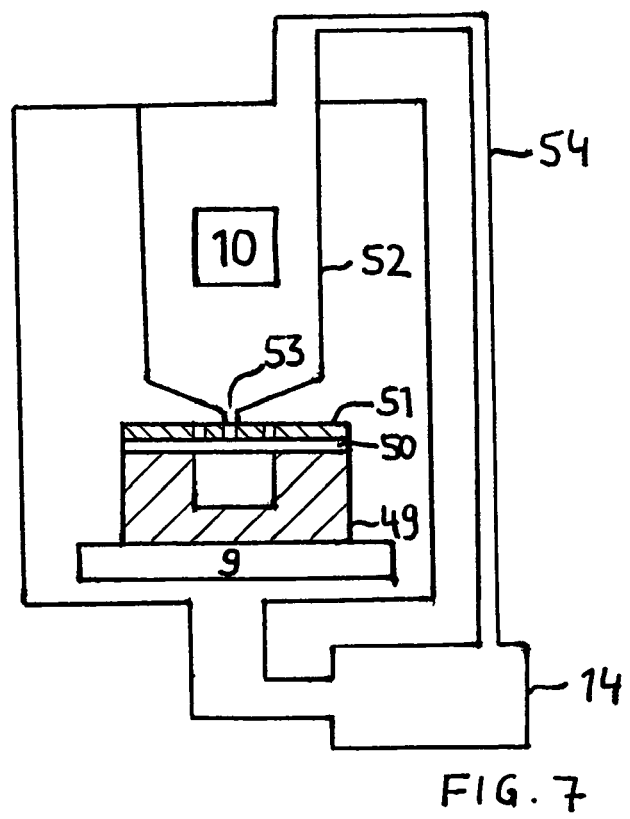
FIG. 7 shows an example for a position resolved measurement of permeation through a polymer sample

FIGS. 6A and 6B shows an alternative construction of a gas container 49 for position resolved measurements. The sample 50 is attached to a gas container 49 by means of a lid 51 made of an impermeable material. In this example the lid 51 has five holes through which the sample 50 can communicate with the mass spectrometer 10. Other numbers and shapes of the openings can be used. Permeation may be studied for the area of one opening position-resolved FIG. 7 shows the arrangement of the gas container 49 with the sample 50 and the lid 51 with respect to the enclosure 52 housing the mass spectrometer. If a hole of the lid 51 are in registry with the aperture 53 of the enclosure 52 of the mass spectrometer 10 gas or vapour molecules from the region of the sample that is located there will preferentially contribute to the partial pressure such creating a contrast picture of the rate of permeation through the sample. The gas container is located on the xyz-stage 9 and can be moved relative to the aperture 53 of the enclosure 52 of the mass spectrometer to expose different areas of the sample to the mass spectrometer. After finishing the measurement at one location, the sample can be shifted relative to the mass spectrometer for the mass spectrometer to face the next location. This way, the rate of permeation can be measured along a line or a two-dimensional pattern.

Figure 8:
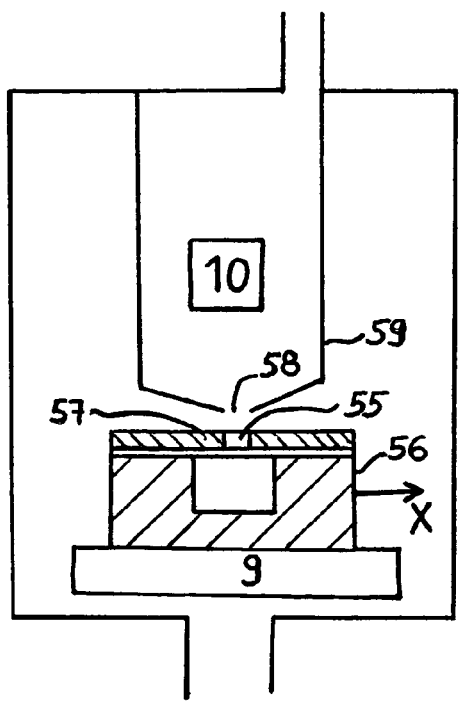
FIG. 8 shows a gas container for position resolved measurement
 A) cross sectional view
 B) top view

FIG. 8 shows the principle of increasing the sensitivity by pumping the interior of the enclosure 52 housing the mass spectrometer 10 through a bypass 54 connected to the ion pump 14.

Figure 9:
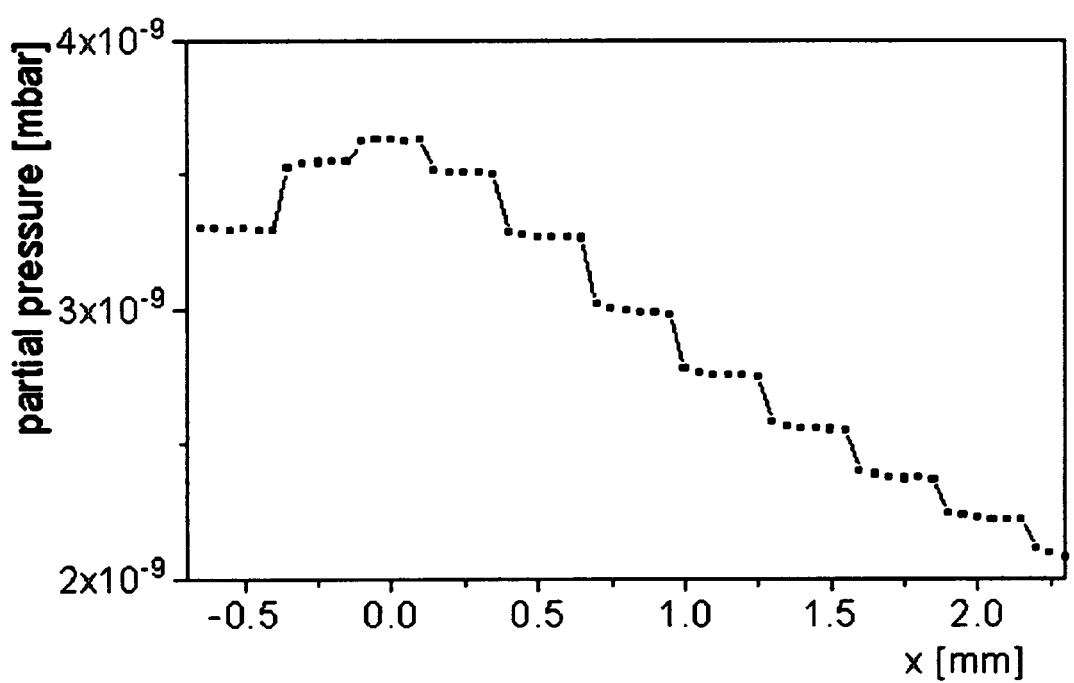
FIG. 9 shows in diagrammatic view the relative position between the mass spectrometer and the gas container for the results shown in FIG. 8

FIG. 9 shows an example for a position-resolved measurement in an arrangement similar to FIG. 8. A polymer sample made of PEN 55 with an exposed area of about 1 mm diameter was mounted on a gas container 56 containing water vapour. Outside the exposed sample area the sample was covered with an impermeable material 57. The gas container 56 was positioned on a xyz-stage 9 closely to the aperture 58 of the enclosure 59 of the mass spectrometer 10. It was then moved across the x-direction in steps of about 0.25 mm. At each location a few data points were taken. FIG. 9 shows the measured partial pressure signal as function of lateral displacement of the sample. At x=0 the sample is in registry with the entrance aperture 58, which leads to a maximum in the partial pressure signal. At x=0.5 mm the exposed sample area of the sample has passed the projection of the entrance aperture 58 completely. The change in the partial pressure signal between x=0 and x=0.5 mm indicates areas of higher and lower permeability.

What is claimed is:

1. A method of measuring the rate of permeation of gases or vapours or mixtures thereof through a test sample comprising:
   providing an amount of gas or vapour in a gas container at a certain vapour or gas pressure;
   arranging the container containing the gas or vapour in a vacuum chamber, which is under vacuum such that the gas or vapour permeating from the container through the test sample communicates with the vacuum chamber under vacuum;
   providing a means to change the relative position between the gas container with the test sample and a mass spectrometer for position resolved measurement of permeation;
   using a mass spectrometer to detect the partial pressure of the gas or vapour after permeation through the test sample; and
   estimating the rate of permeation from the signal measured by a mass spectrometer.

2. The method as claimed in claim 1 wherein the gas container comprises a body, to which one or more test samples are attached forming a seal.

3. The method as claimed in claim 2 wherein one or more of the remaining openings of the body of the gas container are used to accommodate a closing device such as a valve to separate the interior of the gas container from its surrounding the outside.

4. The method as claimed in claim 2 wherein the test sample is sealed to the gas container by pressing the test sample against a sealing face of the gas container with or without using a gasket.

5. The method as claimed in claim 2 wherein the test sample is sealed to the gas container by an adhesive.

6. The method as claimed in claim 2 wherein the test sample is a film.

7. The method as claimed in claim 2 where the temperature of the gas container with the test sample is changed by cooling or heating over a wide temperature range, including cryogenic temperatures.

8. The method as claimed in claim 2 wherein the test sample is made of a polymer, a metal, a ceramic, a biological material or a combination thereof.

9. The method as claimed in claim 1 where the pressure decrease inside the gas container due to permeation is compensated by a flexible device that can change its inner volume.

10. The method as claimed in claim 1 where the gas container is filled with gas or vapour inside a vacuum chamber.

11. The method as claimed in claim 10 where the gas container is filled through a hole with a closing device communicating with a filling chamber filled with a gas or a vapour.

12. The method as claimed in claim 11 where the closing device is operated by means of a tool on a feedthrough.

13. The method as claimed in claim 1 where the partial pressure is measured with the mass spectrometer after the signal has stabilised to a constant value.

14. The method according to claim 1 where the rate of permeation of a gas or vapour is determined from the partial pressure (measured by a mass spectrometer) and calibration against the rate of permeation of gas or vapour of reference samples.

15. The method according to claim 14 where the partial pressure measured from the reference samples is used for calibration.

16. The method according to claim 1 where the experiment is carried out in a high vacuum (HV), ultra-high vacuum (UHV) chamber or extra-high vacuum (XI-IV) chamber under vacuum.

17. The method according to claim 1 where the vapour is water vapour.

18. The method according to claim 1 where the gas container has a movable part for changing the internal volume of the gas container.

19. A method of measuring the rate of permeation of water vapour through a test sample comprising:
    providing an amount of water vapour in a container at a certain relative humidity;
    arranging the container containing the water vapour in a vacuum chamber under vacuum such that the water vapour permeating through the test sample communicates with the vacuum chamber under vacuum;
    using a mass spectrometer to detect the partial pressure of the water vapour after permeation of the water vapour through the test sample;
    providing a means to change the relative position between gas container with test sample and a mass spectrometer; and
    deriving the rate of water vapour permeation from the signal measured by a mass spectrometer.

20. The method as claimed in claim 19 wherein the gas container comprises a body, to which a test sample is attached forming a seal covering an opening of the body of the gas container.

21. The method as claimed in claim 20 wherein one or more of the remaining openings of the gas container are used to house a closing device such as a valve to separate the interior of the gas container from its surrounding.

22. The method as claimed in claim 20 wherein the test sample is a film.

23. The method as claimed in claim 20 wherein the test sample is made of a polymer, a metal, a ceramic, a biological material or a combination thereof.

24. The method according to claim 20 where the effective permeation area of the test sample is a few mm or less in one or two dimensions.

25. The method as claimed in claim 20 where the gas container contains a salt solution, which produces a characteristic relative humidity inside the gas container.

26. The method as claimed in claim 19 where the gas container has a movable part for changing the internal volume.

27. The method as claimed in claim 19 where the gas container is filled with water vapour inside a vacuum chamber.

28. The method as claimed in claim 19 where the gas container is filled through a hole with a closing device inside a vacuum chamber with water vapour.

29. The method as claimed in claim 19 where the gas container containing a reservoir with water vapour is filled with vapour from this reservoir.

30. The method as claimed in claim 19 where the water vapour pressure can be changed.

31. The method as claimed in claim 19 where the temperature of the gas container with the test sample is changed by cooling or heating.

32. The method as claimed in claim 19 where the partial pressure is measured with the mass spectrometer after the signal has stabilised to a constant value.

33. The method according to claim 19 where the rate of permeation of water vapour is determined from the partial pressure as measured by a mass spectrometer and calibration against the rate of permeation of water vapour of reference samples.

34. The method according to claim 19 where the experiment is carried out in an ultra-high vacuum (UHV) chamber under vacuum or in a extra-high vacuum (XHV) chamber under vacuum or in a high vacuum (HV) chamber under vacuum.

35. The method as claimed in claim 19 where the signal to noise ratio of the signal detected by the mass spectrometer is improved by choosing a suitable isotope from $D_2{}^{16}O, D_2{}^{17}O, D_2{}^{18}O, H_2{}^{16}O, H_2{}^{17}O$, and $H_2{}^{18}O$.

36. The method according to claim 19 where the rate of water vapour permeation is determined from the partial pressure as measured by a mass spectrometer and calibration against the partial pressure of one or more samples with a known rate of water vapour permeation.

37. A method for position-resolved permeation measurements at different locations on the test sample comprising: providing an amount of gas or vapour in a gas container at a certain vapour or gas pressure; arranging the container containing the gas or vapour in a vacuum chamber, which is under vacuum such that the gas or vapour permeating from the container through the test sample communicates with the vacuum chamber under vacuum; positioning the test sample close to an enclosure housing a mass spectrometer, where the enclosure has a conical bottom with a hole and a tube attached to the hole; providing a means to change the relative position between the gas container with the test sample and a mass spectrometer in an enclosure for position resolved measurement of permeation; using a mass spectrometer to detect the partial pressure of the gas or vapour after permeation through the test sample; and estimating the rate of permeation position-resolved from the signal measured by a mass spectrometer.

38. An apparatus for measuring the rate of permeation of a gas or vapour including water vapour) including water vapour consisting of:
one or more vacuum chambers,
a gas container which is removable from the vacuum system,
a filling facility,
a mass spectrometer for partial pressure measurement,
a means for changing the relative positions of mass spectrometer and test sample and
a means of transferring the gas container with the test sample.

39. The apparatus according to claim 38 having a gas container that can be filled by means of a filling facility provided in one of the vacuum chambers.

40. The apparatus according to claim 38 with the investigation chamber is under HV, UHV or XHV conditions.

41. The apparatus according to claim 38 where the gas container can be moved between vacuum chambers and removed from the vacuum chambers.

42. The apparatus according to claim 38 where the size of test sample is less than a mm to a few mm in one or two dimensions.

43. The apparatus according to claim 38 where the test sample is clamped or glued to the gas container.

44. The apparatus according to claim 38 where the test sample is a film or a device or an assembly of several parts of a device.

45. The apparatus according to claim 38 where the gas container contains gas or vapour including water vapour.

46. The apparatus according to claim 38 where the pressure of the gas or vapour inside the gas container can be varied by means of a movable part for changing the internal volume of the gas container.

47. The apparatus as claimed in claim 38 where the partial pressure is measured with the mass spectrometer after the signal has stabilised to a constant value.

48. The apparatus according to claim 38 where the rate of permeation is estimated from the measured partial pressure and a calibration against one or more samples with a known rate of permeation.

49. The apparatus according to claim 38 where the temperature of the test sample can be varied.

50. The apparatus according to claim 38 where the mass spectrometer has an enclosure, which can be pumped.

* * * * *